United States Patent [19]

Boyum et al.

[11] Patent Number: 5,333,511
[45] Date of Patent: Aug. 2, 1994

[54] PORTABLE CONTROLLED AIR SAMPLER

[75] Inventors: Gerald A. Boyum, Eugene, Oreg.;
Jon W. Schweiss, Edmonds, Wash.

[73] Assignee: The United States of America as represented by the United States Environmental Protection Agency, Washington, D.C.

[21] Appl. No.: 35,875

[22] Filed: Mar. 23, 1993

Related U.S. Application Data

[63] Continuation-in-part of Ser. No. 579,625, Sep. 7, 1990, abandoned.

[51] Int. Cl.$^5$ .................. G01N 1/24; G06F 15/20
[52] U.S. Cl. .................. 73/864.34; 73/863.01; 73/863.21; 73/863.25; 323/299; 364/496
[58] Field of Search .................. 73/864.34, 864.35, 863.21–863.25, 73/863.31, 863.32, 863.33, 863.01, 31.01, 31.02; 364/496, 480, 483; 340/660, 662, 663; 323/299, 303, 364, 304

[56] References Cited

U.S. PATENT DOCUMENTS

| | | | |
|---|---|---|---|
| 3,673,588 | 6/1972 | Riff | 340/662 X |
| 3,924,471 | 12/1975 | Singer | 73/864.35 |
| 4,287,763 | 9/1981 | Richard | 73/863.21 |
| 4,432,248 | 2/1984 | Lalin | 73/864.34 X |
| 4,521,678 | 6/1985 | Winter | 250/568 X |
| 4,584,887 | 4/1986 | Galen | 73/864.34 X |
| 4,660,422 | 4/1987 | Eads et al. | 73/864.34 X |
| 4,742,716 | 5/1988 | Ruzilka et al. | 73/864.81 |
| 4,800,763 | 1/1989 | Hakkers et al. | 73/863.31 X |
| 4,974,456 | 12/1990 | Ortiz et al. | 73/863.71 X |
| 4,993,271 | 2/1991 | Vargason | 73/863.23 X |
| 5,074,137 | 12/1991 | Harris et al. | 73/31.02 |

FOREIGN PATENT DOCUMENTS

| | | | |
|---|---|---|---|
| 2658739 | 7/1978 | Fed. Rep. of Germany | 73/864.34 |
| 168112 | 10/1983 | Japan | 323/299 |

OTHER PUBLICATIONS

"Over–Under Voltage Protection Circuit"; *IBM Technical Disclosure Bulletin;* vol. 12, No. 12, pp. 2080–2081; May 1970; S. G. Donato, Jr.

*Primary Examiner*—Thomas P. Noland
*Attorney, Agent, or Firm*—Lowe, Price, LeBlanc and Becker

[57] ABSTRACT

A portable analyzer for obtaining samples from a monitored environment during different time intervals includes a pump energized by a rechargeable battery pack for drawing gas from the environment selectively into plural sample holding bags and an impact filter. The pump is programmed to control the time when the gas is drawn from the environment and for controlling the flow to the sample holders so that different ones of the sample holders are responsive to the materials at the same or different times. The pump may respond to electric pulses, causing pulses of air to be supplied to the sample holding bags. The pump derives pulses having a rate directly proportional to the number of pump cycles. The pump may also operate continuously with sampling of the gases being controlled electronically. Operation of the pump is prevented in response to the battery pack voltage dropping to a level such that the voltage is less than a predetermined value, necessary to provide a predetermined flow rate per pump cycle. Operation of the pump is also prevented if the gas flow rate drops below a predetermined level. These prevent features can be manually overridden.

26 Claims, 7 Drawing Sheets

PORTABLE CONTROLLED AIR SAMPLER

RELATION TO CO-PENDING APPLICATION

The present application is a continuation-in-part of co-pending application Ser. No. 07/579,625, entitled "Portable Controlled Air Sampler," filed Sep. 7, 1990. The subject matter of the co-pending application is incorporated herein by reference. The co-pending application is hereby abandoned.

FIELD OF THE INVENTION

The present invention relates generally to obtaining samples from a monitored environment during different time intervals and more particularly to a device including means for drawing gas from the environment into plural sample holders at the same or different times, the gas drawing means being controlled by a programmed timer.

BACKGROUND OF THE INVENTION

Air pollution is generally defined as an unacceptable concentration of one or more air contaminants. Usually air pollution indicates actual or potential adverse health effects for sensitive personnel. Air pollution control programs must, by law in the United States, respond to air pollution with emission reduction requirements. This often means shifting costs of reducing pollution to an emission source or emission sources. Data from air quality monitoring networks are very important, both to describe air pollution problems in terms of geographic extent and magnitude and to measure changes due to emission reductions or increases. High quality air monitoring data ensure that air pollution control programs adequately protect the public health and safety while keeping costs of reducing that pollution as low as possible.

Ideally, there would be full knowledge of air pollutant concentrations at all points and times within geographic areas of concern. However, from a practical standpoint, acquiring such knowledge through continuous monitoring is prohibitively expensive. Sampling and monitoring activities and equipment are expensive. In addition, power and security concerns limit the number of available sites where an agency can gather air quality data at reasonable costs.

Site selection for monitoring is therefore very important. Public confidence in the data is maintained only as long as there is an assurance that the data are representative. It is very difficult, however, to adequately provide an indication of air quality in all areas with one or only a few monitoring sites.

One method of addressing these data gaps is to model an area using selective meteorological and emissions information. This method is frequently used to estimate where and how much air pollution exists. Modeling is a useful technique that relies extensively on the accuracy of collected emissions and meteorological data. Survey sampling and saturation monitoring techniques can be used to augment or verify model values, to define problem areas and to validate monitoring sites.

To provide such sampling, it is desirable for a survey sampler to be portable and capable of relatively long operation, at least up to twenty-four hours. It is also necessary, for certain applications, for the sampler to operate at a flow rate high enough to separate particles below ten micrometers. Such separation, typically requiring flows of five liters per minute, usually involves the use of pumps having appreciable energy requirements. It is also useful to be able to monitor both for particulate material and gaseous pollutants at the same time.

To meet all of these requirements, it is generally not possible to monitor continuously over a twenty-four hour period. Instead, it is necessary to monitor at particular times of greatest interest.

However, because of varying air pollution conditions at different times of the day, it is not acceptable to mix samples taken during different times of a particular day.

Sampling devices have been reported in the prior art, but none teach the apparatus claimed, or achieve the objectives of the current invention. U.S. Pat. No. 5,074,137 issued to Harris, et al. claims a "Programmable Atmospheric Stabilizer." The device disclosed in the Harris patent does not store samples for subsequent analysis, but rather measures an air stream for a particular, pre-determined pollutant. The Harris device cannot be used for quantitative measurements. It only serves to detect whether a particular gas has exceeded a particular threshold. Finally, the Harris device is not portable, and in one embodiment the sampling device is fixed to a storage container or room that contains the material of concern.

U.S. Pat. No. 4,800,763 issued to Hakkers, et al. is directed toward a method and apparatus for drawing and analyzing samples from a fluid stream whereby successive samples of a particular analyte are collected for analysis with the results compared against previous samples. The method disclosed in the Hakkers patent does not comprehend collection of different types of samples during the same procedure. It is not directed toward independent control of the sampling parameters for each sample. The Hakkers patent also does not disclose a portable device.

U.S. Pat. No. 4,432,248 issued to Lalin discloses a portable, battery operated gas sampling device. However, the sampling device of Lalin has only a single gas collection chamber, and the particulate filter is primarily used for trapping particles that interfere with the subsequent collection and analysis of the single gaseous sample. Neither does the Lalin patent disclose independent control of sampling parameters for plural samples. The Lalin patent also teaches away from a low flow warning or shut-down, relying rather on visual means for determining that the particulate filter has become clogged.

It is, accordingly, an object of the present invention to provide a new and improved apparatus for sampling environmental air at diverse times during the day.

It is still another object of the invention to provide a new and improved apparatus for enabling samples of environmental air taken at different times of a day to be separated, for subsequent analysis.

It is also an object of this invention to collect particulate matter for analysis, and over the same time period, collect gaseous samples as well using the same device.

It is also an object of this invention to be able to be able to flexibly program the collection of the gaseous samples so that samples are collected: a) in one sample collection container over one time period and another sample collection container over another time period, or alternatively b) into the plural sample collection containers over the same time periods.

It is another object of the present invention to provide an electrically operated, portable air sampler powered by a battery and that can operate with a constant flow rate, wherein operation of the pump is prevented when the voltage of the battery driving the pump drops below a predetermined level, or when the flow rate of the drawn gas drops below a predetermined level. When the pump is thus prevented from operating, operation of the pump should not automatically resume if the battery voltage or flow rate of the drawn gas again rise above those predetermined levels.

SUMMARY OF THE INVENTION

In accordance with one aspect of the present invention, an apparatus for obtaining a gas sample from a monitored environment during different time intervals comprises plural sample holders in combination with means for drawing gas from the environment and valve means for supplying the drawn gas to the different sample holders. The valve means are preferably programmable on a chronological basis.

In accordance with a further aspect of the invention, an apparatus for obtaining a gas sample from a monitored environment during different time intervals is portable and includes a rechargeable battery pack that energizes a means for drawing gas from the environment. Plural sample holders are preferably provided for receiving materials in the drawn gas. One of these sample holders is for particulates collected from the environment, while others of the sample holders are for gases collected from the environment. The gas drawing means is preferably programmable to control the times when the gas is drawn from the environment and to direct the drawn gas to the sample holders. Gas may be drawn to separate sample holders either simultaneously, in essentially concurrent pulses, or at different times.

In one preferred embodiment, the sample holder for the particulates is upstream of the sample holders for the gases. The apparatus can be operated such that particulates and gases are collected at the same time, such that particulates only are collected with the gas exhausted, or such that gaseous samples only are collected. If plural gaseous samples are being collected, the samples can be collected at the same or different times.

In a preferred embodiment of the invention, operation of the pump is prevented after the battery pack voltage drops below a predetermined level. Operation of the pump does not resume unless a manual override switch is activated. After a fresh rechargeable battery has been installed, normal operation of the pump can be resumed. In similar fashion, operation of the pump is also prevented if the flow rate of the drawn gas falls below a predetermined rate. Operation of the pump does not resume unless a manual override switch is activated.

In accordance with a further aspect of the invention, an electronic clock module including a liquid crystal display and manually controlled programming switches controls the time of day during different days of the week when gas is drawn from the environment into the sample holders.

Still other objects and advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

DESCRIPTION OF THE PREFERRED EMBODIMENTS

The preferred embodiment disclosed herein in FIGS. 1-7 is also disclosed in LRAPA Portable Sampler, Operations Manual, Sampler Model 3.1, Manual Version 1.0a, Lane Regional Air Pollution Authority, Springfield, Oreg., November, 1992. That manual is hereby incorporated by reference.

Figure 2:
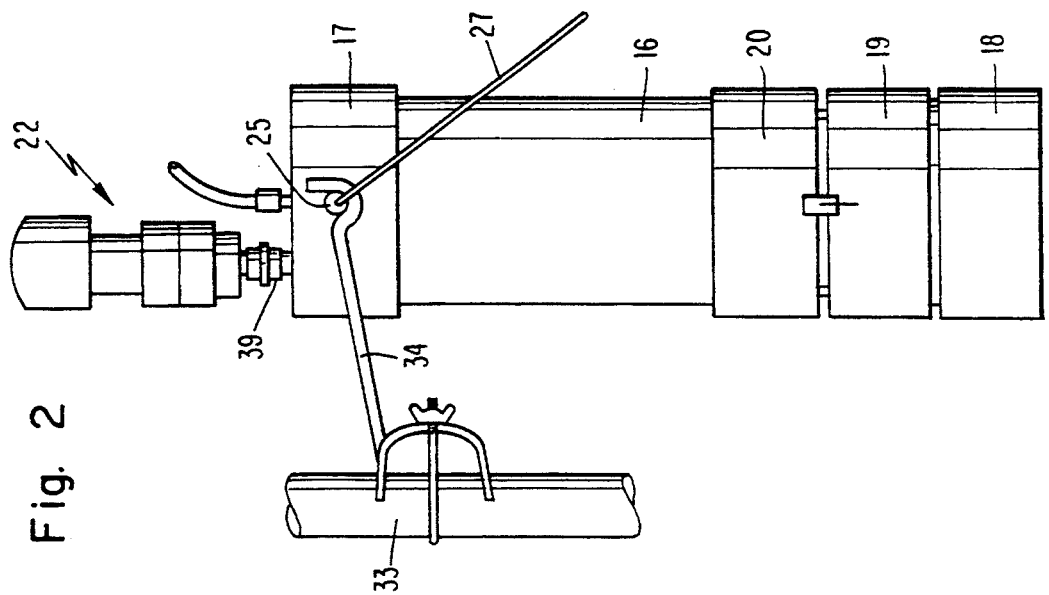
FIG. 2 is a side view of the sampling device illustrated in FIG. 1.
Figure 1:
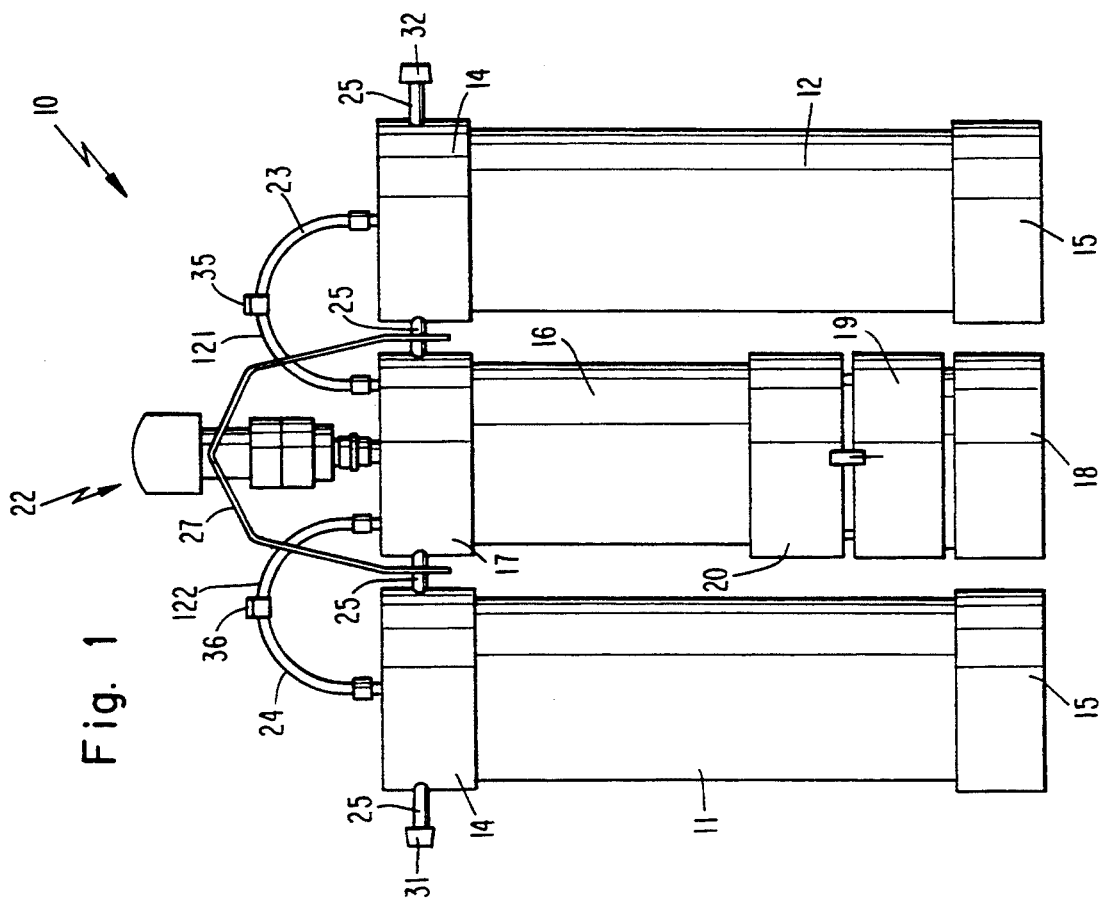
FIG. 1 is a front view of a preferred embodiment sampling device of the present invention including a double-bag sampling configuration.
Figure 3:
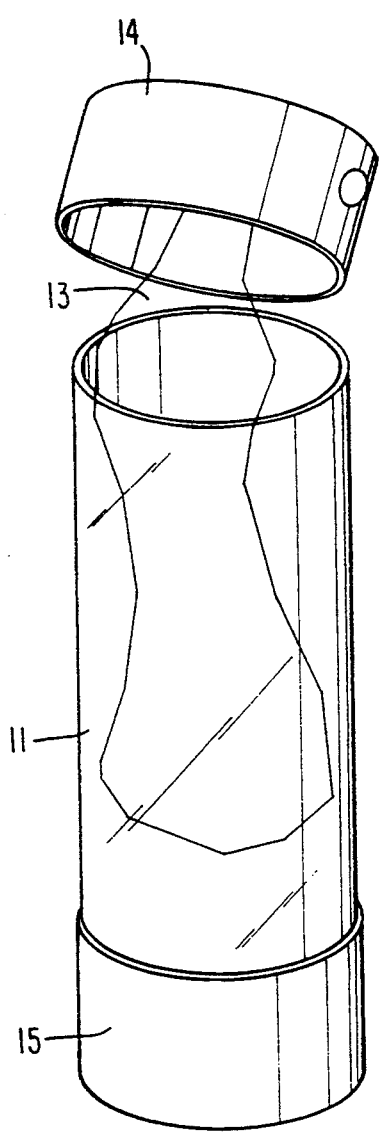
FIG. 3 shows a canister from the sampling device of FIG. 1 shown in combination with a sample bag partly removed from a canister.

Reference is now made to FIGS. 1-3 of the drawings wherein the preferred embodiment of the sampling device 10 of the invention is illustrated as including cylindrical canisters 11 and 12, each including an interior separate air sample receiving bag 13, selectively attached by suitable means (not shown) to top end caps 14 of the canisters. Receiving bag 13 is a plastic bag impervious to passage of gas through the plastic. Receiving bag 13 is, for example, a TEDLAR bag made from material manufactured by E.I. DuPont de Nemours & Co., Inc., Wilmington, Del. Top end caps 14 are fixed on canisters 11 and 12, as are bottom end caps 15. Canisters 11 and 12 are mounted on opposite sides of a central cylinder 16. Central cylinder 16 includes end caps 17 and 18, a battery pack 19 and a flow controller 20. Flow controller 20 is energized by rechargeable lead acid batteries in battery pack 19. Extending upwardly from and fixedly connected to end cap 17 by upwardly extending quick disconnect 39, as is known in the art, is pre-separator and filter assembly 22 through which air samples are drawn from the environment for distribution into sample receiving bags 13 in canisters 11 and 12 by way of tubes 23, 24, 121 and 122. Tubes 23 and 24 provide fluid flow paths from central cylinder 16 to the sample receiving bags 13 in canisters 11 and 12.

Canisters 11 and 12 are connected to cylinder 16 by way of a bar 25 that extends through holes in end caps 14 and 17. Bar 25 does not prevent canisters 11 and 12 from being removed from end cap 17 and central cylinder 16. Wire bale handle 27 fits over and is attached to bar 25. Opposite ends of bar 25 extend outwardly from end caps 14 on canisters 11 and 12, respectively. Removable end caps 31 and 32 are screwed onto threads on the ends of bar 25.

As can be seen in FIG. 2, the entire sampler assembly can be fixedly mounted in use, to a stationary post or mast 33 by a hanging bracket 34 which supports bar 25. Bag module disconnect valves 35 and 36 are respectively provided between tubes 23 and 121 and between tubes 24 and 122, so that one canister can be removed and replaced without affecting the operation of the sampling device while flow continues to the other bag.

Figure 4:
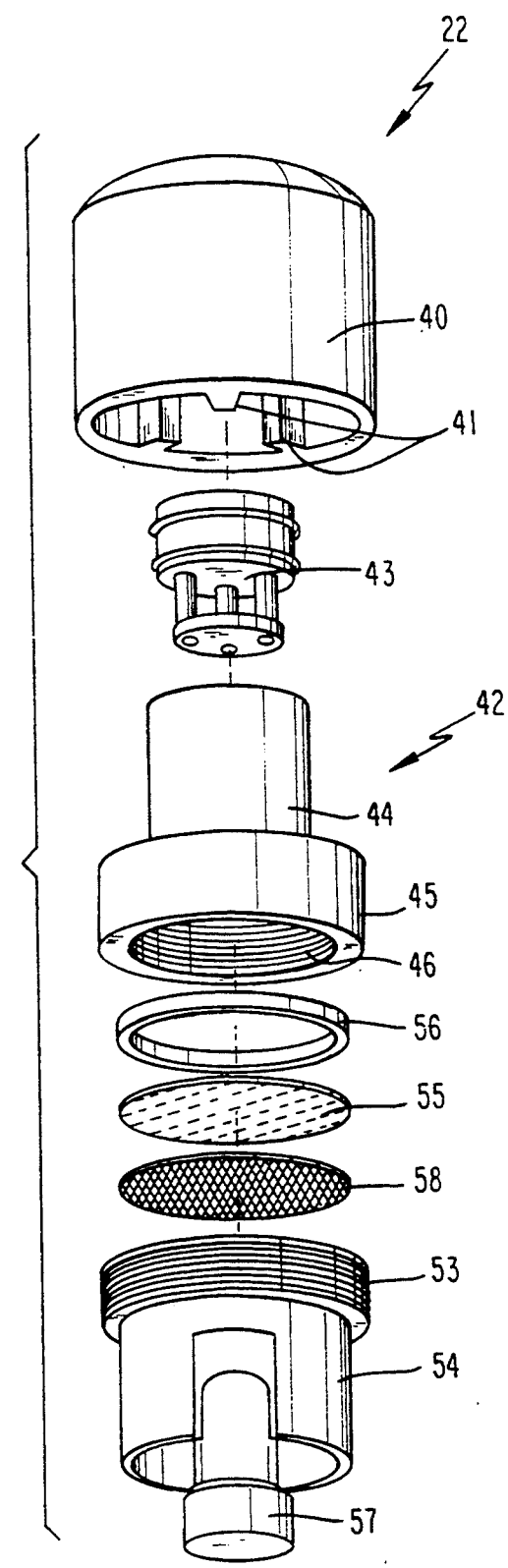
FIG. 4 is an exploded view of a pre-separator and filter assembly from the sampling device of FIG. 1.

Pre-separator and filter assembly 22 is illustrated in FIG. 4 as including a rain cap 40 into which is fitted pre-separator adapter 42 that receives impactor 43. Rain cap 40 has spacers 41 for enabling air to be sucked from beneath the rain cap 40 and around the impactor 43. Before the pre-separator and filter assembly 22 is assembled for use, impactor 43 is lightly greased by evaporating on it a suspension of for example 1-inch of Apiezon M grease in 100 ml of hexane. Apiezon greases are made by Biddle Instruments, Blue Bell, Pa. Particulate matter larger than that to be sampled is removed from the air stream as the air is drawn through the rain cap 40, past the spacers 41, and around the impactor 43. Impactor 43 fits into the interior of cylinder 44 of pre-separator adapter 42. Pre-separator adapter 42 includes a ring 45 that is coaxial with and has a greater radius than cylinder 44. The interior surface of ring 45 includes threads 46 that engage threads 53 on the exterior of a filter holder 54. A filter 55, preferably a 47 mm diameter filter, is secured in place by filter holder 54 with the aid of a slip ring 56 that fits into preseparator adapter 42. A drain disk 58 fits under filter 55 in the interior of filter holder 54. Slip ring 56 prevents filter 55 and drain disk 58 from being damaged when pre-separator adapter 42 and filter holder 54 are screwed together. Drain disk 58 protects filter 55 from damage while air is flowing through pre-separator and filter assembly 22.

In the preferred embodiment, particles larger than those to be monitored are filtered out by the path of the air stream through preseparator assembly 42 and around impactor 43. The mesh of filter 55 and the flow rate of air drawn from the atmosphere by a pump 100 (shown in FIGS. 6 and 7 and described below) are selected such that particulate matter with diameter less than or equal to 10 micrometers ($PM_{10}$) which is suspended in the air is drawn around impactor 43 and deposited on filter 55. It has been found that $PM_{10}$ will be properly suspended in the drawn air stream if the pump 100 is set to produce a flow rate of 5 liters per minute through filter 55. It has been found that $PM_{10}$ will be trapped on filter 55 when filter 55 is an aerosol filter such as that made by the Nuclepore Corp. of Pleasanton, Calif. Filter holder 54 includes a central, downwardly extending quick disconnect 57 which mates with the upwardly extending quick disconnect 39 mounted on the end cap 17 of central cylinder 16, to provide a fixed mount for pre-separator and filter assembly 22 and to permit easy and quick removal of pre-separator and filter assembly 22 from central cylinder 16.

Figure 5:
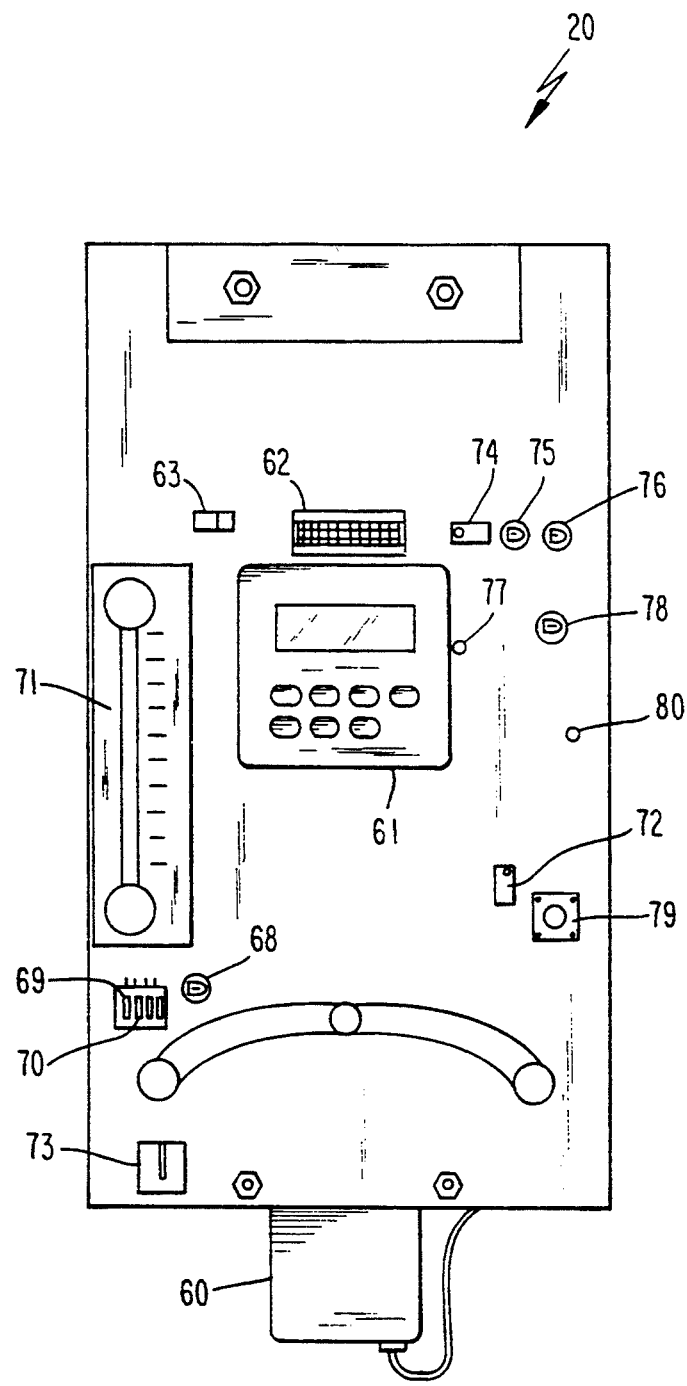
FIG. 5 is a front view of a flow controller for the sampling device of FIGS. 1-4.

Reference is now made to FIGS. 5 through 9 which illustrate the operation of flow controller 20. FIG. 5 is the front face of flow controller 20. FIG. 5 shows brushless DC pump motor 60, which operates a twin cylinder diaphragm pump 100 whose operation is described below. The front face of flow controller 20 includes indicators 62, 71, 77, and 80, programmable timer 61, manually activated connector 63, power connector 73, keys 68, 75, 76, and 78, screws 72 and 74, and switches 69, 70, and 79 which are turned to control certain parameters for the flow controller 20. Flow controller 20 has a programmable timer 61, as for example an UNCO-2, which controls cycling of the sampling device 10, and allows up to six sampling periods to be preprogrammed over twenty-four hours, or over the course of a week. An elapsed time accumulator 62 on flow controller 20 totals the length of time, in hours and minutes, that pump 100 has been running.

Flow controller 20 has two operative function switches 69 and 70. Function switch 69 is the power switch for sampling device 10. Function switch 70 activates or deactivates a pulse mode for sampling. The pulse mode is the mode used for collecting a series of small pulses of air into air sample receiving bags 13. A series of small pulses is collected in order to ensure that a representative sample of the ambient air is obtained for determination of one or more of the gaseous components. (The function switch assembly used in the preferred embodiment is a commercially available device with four switches, only the first two of which are operational in the course of using the invention.)

When the sampling device 10 is being operated in pulse mode, it is necessary to adjust both the duration of each pulse and the frequency of the pulses in order to obtain a representative air sample and to fill the air sample receiving bags 13 to no more than 80-90% of capacity. The optimum combination of the pulse duration and pulse frequency parameters is usually determined through trial and error in laboratory tests prior to installing the sampler at a site. Duration of the pulse is set in terms of cycles of the pump motor 60. This is done by using a pulse duration jumper assembly 63. Pulse duration jumper assembly 63 has a conducting bar which can be placed into any one of 4 pairs of holes to control duration of the pulse. The pairs of holes define pulse durations of 4, 8, 16, and 32 cycles, respectively. The frequency of the pulses is controlled by a pulse-mode frequency adjustment 68. In a preferred embodiment, the frequency of each pulse can be varied between 1 pulse in 5 seconds and 1 pulse in 20 seconds.

A flowmeter (rotameter) 71 on flow controller 20 indicates the flow rate of air through the sampling device 10 in liters per minute. The flow rate is adjusted using the flowrate adjustment 72, as described below. Flow sensor alignment adjustments 74-76 align pressure sensor 113 (shown in FIGS. 6, 7, and 8 and described below) with other electrical system components in the sampling device 10. The flow sensor alignment adjustments 74-76 are not generally changed during operation of the sampling device 10.

In order to protect the pump 100, and ensure that the $PM_{10}$ remains suspended until trapped by filter 55, the air flow cannot drop below limits set for a particular monitoring study. A low flow indicator 77 lights when air flow through the system has dropped below such a preset lower limit. The desired lower air flow limit is set by adjusting a low flow cut-off adjustment 78. When low flow indicator light 77 is lit, the sampling device has turned off and can only be restarted by pressing reset switch 79.

Pump 100 will also be damaged if the voltage of battery 19 drops below a predetermined value, as for example, 10.3 volts. A low battery indicator 80 lights when the voltage drops below the minimum required voltage. When the low battery indicator 80 is lit, the sampling device has turned off and can only be restarted by pressing reset switch 79.

A 12 volt battery power connector 73 conducts power from the battery 19 to the sampling device 10 and may comprise a standard phone plug-in jack.

Figure 6:
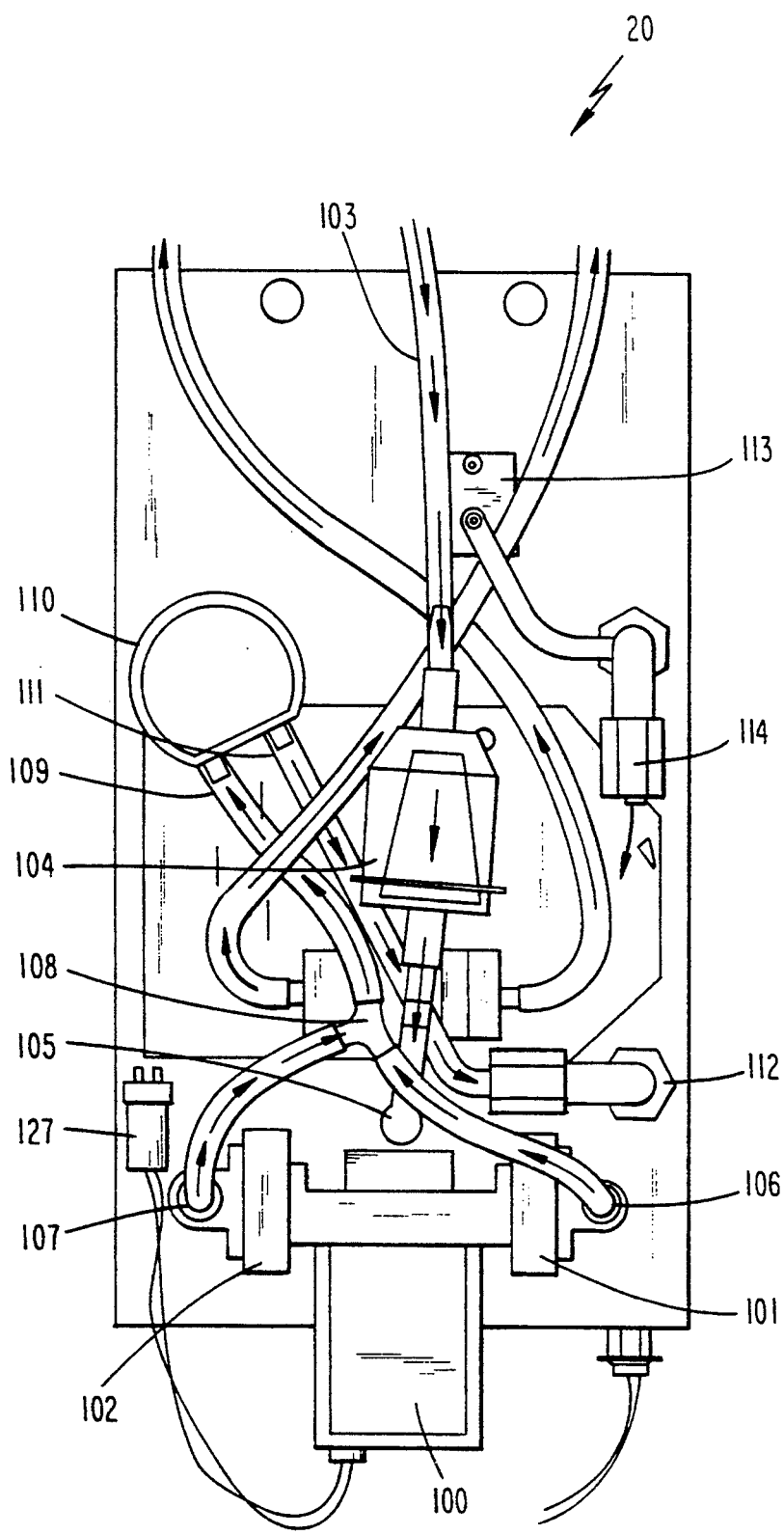
FIG. 6 is a rear view of the flow controller illustrated in FIG. 5, shown configured for collection of particulate material.

FIG. 6 is a rear view of flow controller 20 configured for sampling of particulate matter generally, and preferably, $PM_{10}$. The figure shows a twin cylinder diaphragm pump 100 driven by the brushless DC motor 60 of FIG. 5 and including diametrically opposed cylinders 101 and 102. Pump 100 and its associated brushless DC motor 60 are, for example, a Brailsford Type-T double acting diaphragm pump with magnetically commutated motor made by Brailsford & Co., Inc., Rye, N.Y. Environmental air is drawn by pump 100 through filter 55 of FIG. 4, passing through quick disconnect 39 into inlet tube 103, through pump inlet filter 104 (which protects pump 100 from damage if the sampler is operated without pre-separator and filter assembly 22) and then into pump inlet 105. The drawn air is pumped from cylinder 101 to tube 106 and from cylinder 102 to tube 107. Tubes 106 and 107 converge at T-connector 108 that connect to tube 109. Tube 109 is connected to a pulse dampener 110. The outlet from pulse dampener 110 is connected by tube 111 to the flowmeter 71 of FIG. 5 at flowmeter inlet 112. Flowmeter 71, of conventional design, provides a visual indication of the flow rate of gas flowing through filter 55. Flowmeter 71 includes a free float and linear scale to provide a visual indication of the flow rate of environmental (atmospheric) air flowing through filter 55 and into conduit 103. A pressure sensor 113, connected to flowmeter 71, senses the air flow rate, and controls the speed of pump motor 20 to maintain a constant flow rate. Gases exhausting from flowmeter 71 are then exhausted to the atmosphere at flowmeter output 114.

Figure 7:
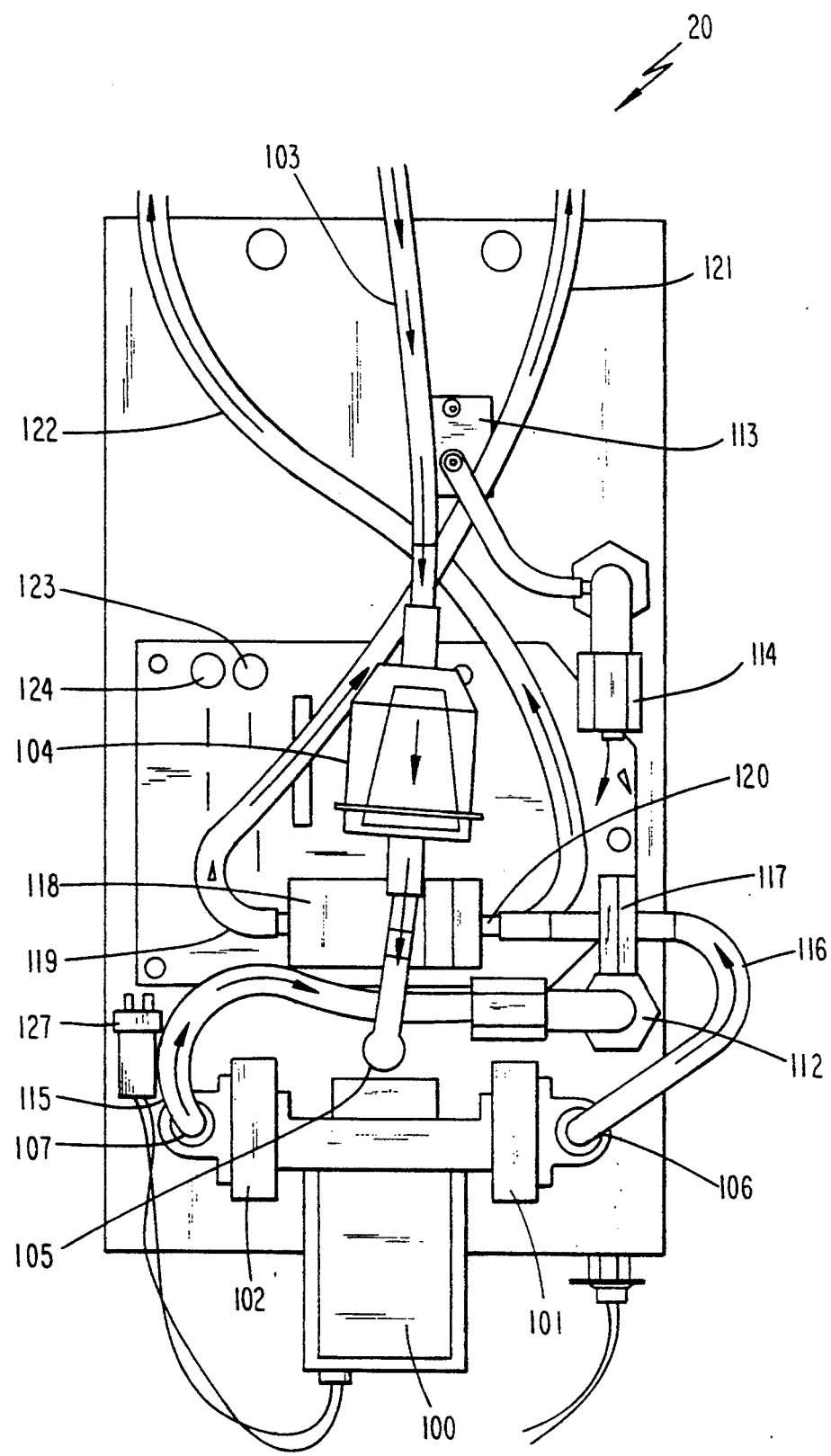
FIG. 7 is a rear view of the flow controller illustrated in FIG. 5, shown configured for collection of gaseous samples.

FIG. 7 shows the back of flow controller 20 configured for gas sampling. Air is drawn into pump 100 and pumped out to outlets 106 and 107 in the same manner described for FIG. 6. In this configuration, most of the drawn air is discharged continuously and evenly from cylinder 102 through pump outlet 107 and tube 115 to flowmeter inlet 112 of flowmeter 71. Flowmeter 71 and pressure sensor 113 function in the same way as described above, and the air passing through flowmeter 71 is likewise exhausted through flowmeter output 114.

Air from pump outlet 106 is conducted through tube 116 to a solenoid valve inlet 117 of a solenoid valve 118. Solenoid valve 118 includes a pair of diametrically opposed output ports 119 and 120 (output port 120 is directly behind input port 117). Output ports 119 and 120, respectively, are connected to tubes 121 and 122, respectively, which, in turn, are respectively connected to inlets of air sample receiving bags 13 in canisters 11 and 12.

Solenoid valve 118 is controlled by programmable timer 61 so that gas supplied to it via tube 116 alternately flows to tubes 121 and 122. Operation of solenoid valve 118 may be controlled by programmable timer 61 such that during a first interval air pumped by pump 100 to solenoid valve 118 from tube 116 flows to canister 11 by way of tube 122. During a second, mutually exclusive time period air pumped by pump 100 is directed by solenoid valve 118 to flow from tube 116 to tube 122, then to air sample receiving bag 13 in canister 12. Visual indications of which canister 11 or 12 is receiving an air sample at any particular time period and of the canister which most recently received a sample are provided by LEDs 123 and 124, which are respectively activated in response to the sample bags in canisters 11 and 12 being supplied with the sample gases.

Pulse mode switch 70 of flow controller 20 must be turned on during the entire period that gas sampling is taking place. However, the opening of solenoid valve 118, and discharge of drawn gas air from cylinder 106 through tube 116, solenoid valve 118, and tubes 121 and 122 is controlled by the pulse duration assembly 63 and pulse-mode frequency adjustment 68 as described above. Thus, over any one sampling time period, only sufficient gas is collected to fill the gas receiving sample bags 13.

Solenoid valve 118 can be programmed by programmable timer 61 so that it is activated at different times during different 24-hour intervals. For example, solenoid valve 118 can be programmed so that on Monday air samples are supplied to air sample receiving bag 13 in canister 11 between 10 AM and 1 PM while air is supplied to air sample receiving bag 13 in canister 12 on Monday between 2 PM and 7 PM. However, on Saturday of the same week, solenoid valve 118 could be programmed so that air flows to canister 11 between 8 AM and 11 PM and to canister 12 between 3 PM and 6 PM.

Sampling device 10 can be used to determine total concentrations both of $PM_{10}$ and two samples of gases. For $PM_{10}$, elapsed time accumulator 62 shows the elapsed time for an entire sampling sequence. Multiplying that elapsed time by the flow rate known from flowmeter 71 gives a total volume of air passing through sampling device 10. The weight of $PM_{10}$ collected on filter 55 can be determined by standard techniques. Dividing the weight of $PM_{10}$ collected on filter 55 by the total volume of gas passing through sample device 10 gives a concentration of particulate matter.

Programmable timer 61 shows the elapsed time gas samples are being supplied to each of canister 11 and canister 12. Multiplying each of these times by the flow rate known from flowmeter 71 gives a total volume of air sampled for the air in each canister. When the pulse frequency and duration have been determined, as disclosed above, the total amount of gas going into canisters 11 and 12 is also known. Pollutant concentrations in canisters 11 and 12 may then be determined by gas chromatography or other quantitative methods known in the art.

Brushless DC pump motor 60 is connected to flow controller 20 by a connector 127. Connector 127 includes two female contacts adapted to receive two male contacts connected to a two wire cable connected to brushless DC pump motor 60.

In another preferred embodiment of the invention, sampling device 10 can be configured: 1) for simultaneous collection of particulates such as $PM_{10}$ as well as gases; 2) for filling of canisters 11 and 12, either concurrently or simultaneously; and 3) for continuous operation rather than pulsed operation of pump motor 60. For example, one can collect two 4- or 8-hour gas samples, concurrently or simultaneously with each other, and concurrently with a 24-hour $PM_{10}$ sample.

Figure 8:
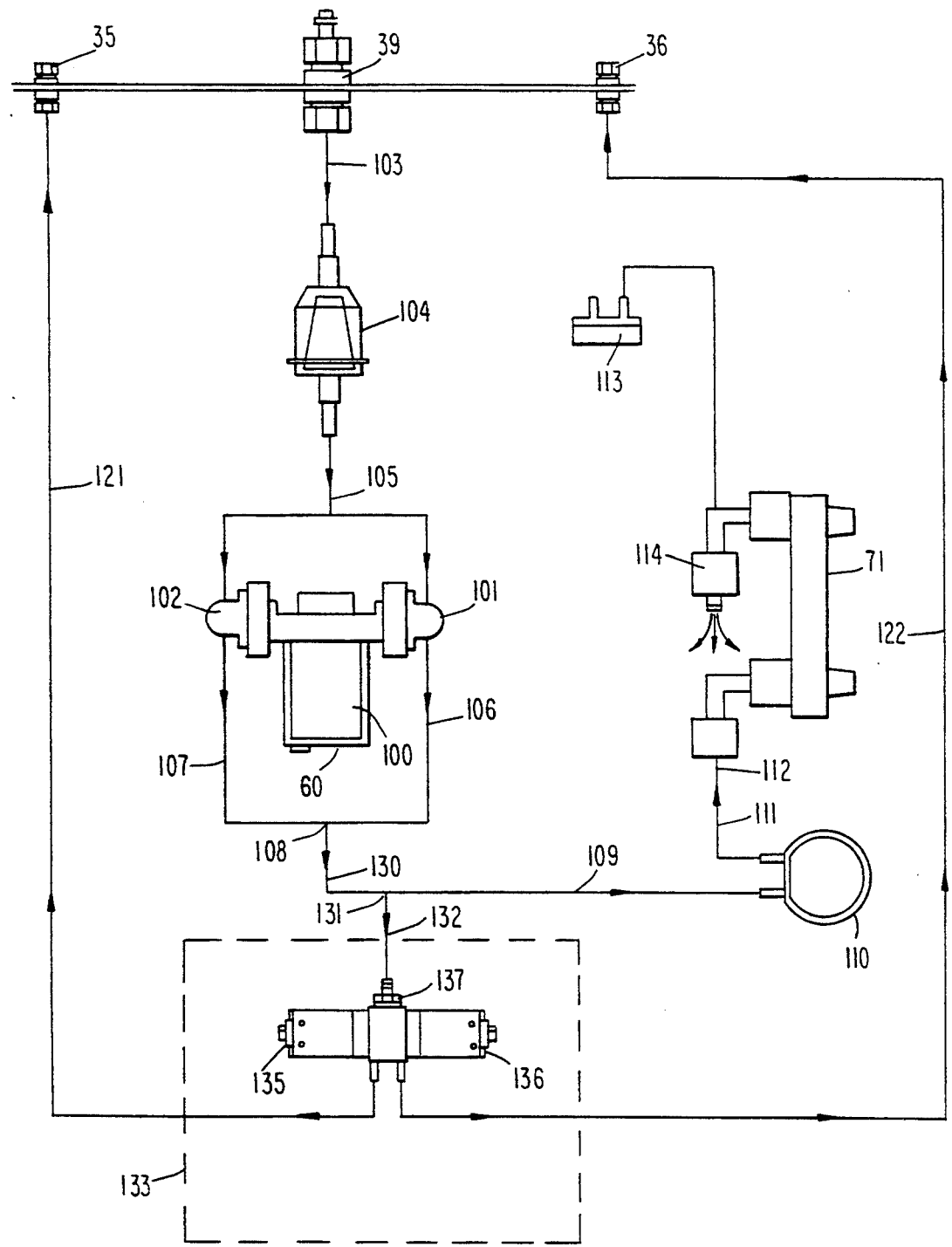
FIG. 8 is a schematic flow diagram showing the sampling device configured both for the collection of particulate material and gaseous samples.
Figure 9:
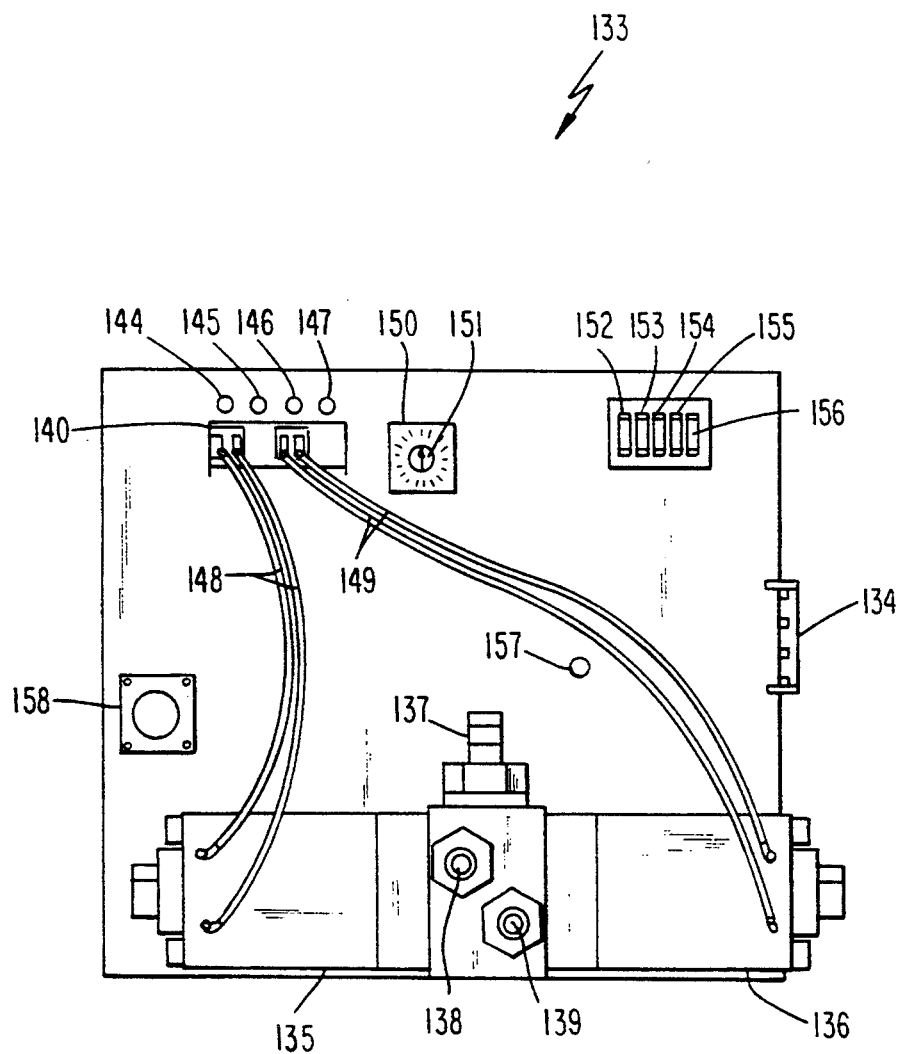
FIG. 9 is an enlarged view of the valve driver board of FIG. 8.

A schematic flow diagram for this preferred embodiment is shown in FIGS. 8 and 9. Air is drawn into pump 100 in the same manner described for FIG. 6. Outputs 101 and 102 from pump 100 carry pumped air into tubes 106 and 107 which converge at T-connector 108, as described above. The output from T-connector 108 discharges into tube 130 which connects to another T-connection 131. One output from T-connection 131 discharges to tube 109 through pulse dampener 110, through flowmeter 71, and then out to the atmosphere at flowmeter output 114, as described above. The other output from T-connection 131 discharges to tube 132. Tube 132 leads to a valve driver board 133 as shown in FIGS. 8 and 9. Valve driver board 133 controls two solenoid valves 135 and 136 which substitute for the single solenoid valve 118 described above. Use of the two solenoid valves 135 and 136 makes it possible to fill canisters 11 and 12 over the same time period, or during overlapping time periods. Valve driver board 133 also replaces the pulse mode operation of pump 100 and pump motor 60 described above. Pump 100 and pump motor 60 can operate continuously while valve driver board 133 controls the pulsed discharge of gas to containers 11 and 12.

Valve driver board 133 is adapted to be plugged into a connector (not shown) of flow controller 20 by a 4-pin connector 134. The two solenoid valves 135 and 136 have a common input port 137. Common input port 137 supplies gas to both solenoid valves 135 and 136 at the same time.

In the preferred embodiment shown in FIG. 9, each of the solenoid valves 135 and 136 are biased closed by constant back-pressure generated by the continuous operation of pump 100. Valve driver board 133 regulates the time periods when solenoid valves 135 and 136 are opened, frequency of openings and the duration of each opening. A solenoid connector assembly 140 controls the time periods when solenoid valves 135 and 136 are opened and the frequency of the openings. Dual In-line Package (DIP) switches 152-155 regulate the duration of each valve opening.

Solenoid connector assembly 140 is a 4-position plug and switch assembly with 4 places for receiving control leads 148 and 149 from solenoid valves 135 and 136. Control leads 148 and 149 can be plugged into any of the 4 positions of solenoid connector assembly 140. The solenoid connector assembly 140 is connected to the programmable timer 61 on flow controller 20 through female connector 134.

Each time programmable timer 61 is switched off, one of the 4 positions of solenoid connector assembly 140 is primed for activation, in sequence. The position primed to be activated is indicated by one of 4 signal lights 144-147 above the 4 positions of the solenoid connector assembly. When the programmable timer 61 of flow controller 20 is next switched on, the next position of solenoid connector assembly 140 in sequence is activated. If one of solenoid leads 148 and 149 is plugged into the activated position of solenoid connector assembly 140, the respective solenoid valve 135 or 136 is available for intermittent opening and closing.

The actual opening of solenoid valves 135 and 136 is controlled by circuits on the valve driver board 133 which provide for different frequencies of opening, and different durations of opening. The frequency of opening is controlled by a tunable intervalometer 150 adjusted by means of a rotary switch 151. Rotary switch 151 can be turned to adjust the frequency of opening of solenoid valve 135 or 136 between one time per second and one time per 16 seconds, in increments of one in one second.

DIP switches 152-155 are used to regulate the duration of opening for solenoid valve 135 or 136 each time one of the solenoid valves is open. The first 4 DIP switches have the following time interval values: 25 milliseconds (152), 50 milliseconds (153), 100 milliseconds (154), and 200 milliseconds (155). The duration for each opening of one of the solenoid valves is determined by the sum of the values of DIP switches 152-155 set in the down, or "off" position. Thus, for example, if DIP switches 152 and 155 are set in the off position, and DIP switches 153 and 154 are set in the on position, the solenoid valve activated by solenoid connector assembly 140 and tunable intervalometer 150 will be opened for 225 milliseconds (25+200) per cycle. DIP switch 156 is the on-off power switch for the valve driver board 133. Valve driver board 133 also has a cycle indicator 157 to show when one of the solenoid valves 135 or 136 is open, and a manual sequence advance button 158 which can be used to override solenoid connector assembly 140 and activate the next position of the solenoid connector assembly independently of programmable timer 61.

When solenoid valve 135 or 136 is open, outputs 138 or 139, respectively, discharge gas to tubes 121 or 122, as shown in FIG. 8. Both solenoid valves 135 and 136 open simultaneously if control leads 148 and 149 are attached to the same position of solenoid connector assembly 140.

In the preferred embodiments, an actual flow rate of five liters per minute is necessary to assure that $PM_{10}$ remains suspended in the drawn air, passes by impactor 43 and is retained on filter 55. To assure a five liter per minute flow rate, the sampling device 10 must be calibrated for each sampling project to account for differing air temperatures and atmospheric pressures, due, for example, to differences in elevations where the equipment is operating. The unit flow per pump cycle count is established using the reading from flowmeter 71 and a stop watch.

After each sampling, i.e., when the air sample receiving bags 13 in canisters 11 and 12 have both been filled, the apparatus must be serviced and set up for the next sampling cycle. Servicing includes removing each of canisters 11 and 12, then removing filter holder 54 and filter 55 therein. The air sample receiving bags 13 in canisters 11 and 12 and filter 55 are then changed.

To remove canisters 11 and 12, tubes 23 and 24, respectively connected by disconnect valves 35 and 36 to tubes 121 and 122, are disconnected from tubes 23 and 24 after disconnect valves 35 and 36 have been closed. Disconnect valves 35 and 36 are then disconnected from tubes 121 and 122. Canisters 11 and 12 are then removed from bars 25 and new modules with new bags are then mounted on the bars. Disconnect valves 35 and 36 are then opened, permitting operation in accordance with the programmed times established in programmable timer 61. The samples in air sample receiving bags 13 within canisters 11 and 12 are taken to a laboratory for analysis in accordance with standard protocol as is filter 55.

The battery in battery pack 19 is also changed at that time, if low battery indicator 80 is lit. The battery in battery pack 19 does not need replacing each time that canisters 11 and 12 and filter 55 are changed.

While there have been described and illustrated specific embodiments of the invention, it will be clear that variations in the details of the embodiments specifically illustrated and described may be made without departing from the true spirit and scope of the invention as defined in the appended claims. For example, plural impact sample holders can be controlled on a sequential basis in accordance with principles similar to those described for the air sample receiving bags within canisters 11 and 12.

I claim:

1. Apparatus for obtaining gas samples from a monitored environment during differing time intervals comprising plural sample holders, means for drawing gas from the environment, valve means for supplying the drawn gas to the different sample holders at mutually exclusive times, and means for programming the valve means on a chronological basis, said programming means including means for independently controlling for each of the different sample holders the time when said valve means starts supplying drawn gas to the sample holder, the time when said valve means stops supplying drawn gas to the sample holder, and the sample interval between when said valve means starts and stops supplying said drawn gas to the sample holder.

2. A portable device for obtaining samples from a monitored environment during differing time intervals comprising a rechargeable battery pack, means energized by the battery pack for drawing gas from the environment, plural sample holders for materials in the drawn gas, one of said sample holders being for particulates in the environment, others of said sample holders being for gases in the environment, and said gas drawing means including programmed means for controlling the time the gas is drawn from the environment and for controlling the flow to the sample holders so that different ones of the sample holders are responsive to the materials at different times, said programmed means including means for independently controlling for each of the different sample holders the time when said drawing means starts supplying drawn gas to the sample holder, the time when said drawing means stops supplying drawn gas to the sample holder, and the sample interval between when said drawing means starts and stops supplying said drawn gas to the sample holder.

3. The device of claim 2 wherein the sample holder for the particulates is upstream of the sample holders for the gases, and the flow of gas to the sample holders for the gases is controlled so that the gas flows into only one of the gas sample holders at a time.

4. The device of claim 3 wherein said programmed means includes means for controlling said drawing means to direct gas drawn through said particulate sample holder at mutually exclusive times to one of said gas sample holders or back to the monitored environment.

5. The device of claim 3 wherein said programmed means includes means for controlling said drawing means to direct gas drawn through said particulate sample holder over the same time period or back to the monitored environment.

6. The device of claim 2 wherein the gas drawing means includes a pulsed cycling pump energized by the battery pack, the pump deriving pulses having a rate directly proportional to the number of cycles of the pump in drawing gas from the environment, and means responsive to the pulses for displaying an indication of the number of cycles of the pump in drawing gas from the environment.

7. The device of claim 6 wherein the gas drawing means includes means energized by the battery pack for deriving constant amplitude DC voltage pulses having predetermined interpulse intervals, the pump being responsive to the pulses to be driven at a rate determined by the rate of the pulses.

8. The device of claim 7 wherein the gas drawing means includes means for preventing operation of the pump in response to the battery pack voltage dropping to a level such that the amplitude of the pulses is less than a predetermined value.

9. The device of claim 8 further including means for visually signalling that the pump is not operating because the amplitude of the pulses is less than the predetermined value.

10. The device of claim 8 further including means for continuing to prevent operation of the pump after the battery pack voltage has initially dropped to below said level even though the battery pack voltage thereafter rises to a level such that the amplitude of the pulses would not be less than the predetermined value.

11. The device of claim 10 further including manually activated means for overriding the means for continuing to prevent pump operation.

12. The device of claim 2 wherein the programmed means includes an electronic clock module including a liquid crystal display and first and second manually controlled programming switches for controlling the time of day during different days of the week when the gas is drawn from the environment.

13. The device of claim 2 further including means for deriving first and second indications respectively representing voltage being in excess of and less than a predetermined value necessary to provide proper operation of the means for drawing, and means responsive to the indications for controlling the flow of current from the battery pack to the means for drawing so that (a) the battery pack initially supplies current to the means for drawing and continues to supply current to the means for drawing while the first indication is derived until the second indication is initially derived and (b) the flow of current from the battery pack to the means for drawing is prevented in response to derivation of the second indication and is prevented thereafter even though the battery pack voltage increases above the predetermined value.

14. The device of claim 2 wherein said programmed means includes means for controlling said drawing means to repeatedly start and stop the supplying of drawn gas to a first of said gas sample holders for programmed sampling intervals and means for independently controlling the time interval between each such sampling interval.

15. The device of claim 14 wherein said programmed means includes means for controlling said drawing means to direct a drawn gas to a second of said sample holders during the time interval between sampling intervals of said first gas sample holder.

16. The device of claim 14 wherein said programmed means includes means for controlling said drawing means to direct a drawn gas to a second of said sample holders at the same time as directing the drawn gas to the first of said sample holders.

17. The device of claim 2 wherein the gas drawing means includes a pump energized by a battery pack, the pump operates continuously, and the gas is admitted to the gas sample holders through programming of solenoid valves.

18. The device of claim 17 wherein the gas drawing means includes means energized by the battery pack for controlling solenoid valves to be open with different frequencies and intervals thereby filling the gas sample holders simultaneously, concurrently or at mutually exclusive time periods.

19. The device of claim 18 wherein the gas drawing means includes means for preventing operation of the pump in response to the battery pack voltage dropping to a level that is less than a predetermined value.

20. The device of claim 19 further including means for continuing to prevent operation of the pump after the battery pack voltage has initially dropped below said level even though the battery pack voltage thereafter rises to a level such that the amplitude of the pulses would not be less than the predetermined value.

21. The device of claim 20 further including manually activated means for overriding the means for continuing to prevent pump operation.

22. The device of claim 17 wherein the gas drawing means includes means for preventing operation of the pump in response to the gas flow rate dropping to a level that is less than a predetermined level.

23. The device of claim 22 further including manually activated means for overriding the means for continuing to prevent pump operation.

24. The device of claim 2 wherein the programmed means includes an electronic clock module including a liquid crystal display and programming switches for controlling the time of day and the days of the week when the gas is drawn from the environment.

25. The device of claim 2 wherein said programmed means includes means for controlling said drawing means to maintain a specified flow setting by measuring the drop in air pressure at the outlet of the flowmeter and by compensating for reasonable changes in ambient temperature and pressure.

26. Apparatus for obtaining gas samples from a monitored environment during differing time intervals comprising plural sample holders, means for drawing gas from the environment, means for filtering particles from the drawn gas, valve means for supplying the drawn gas to the different sample holders, and means for programming the valve means on a chronological basis, said programming means including means for independently controlling for each of the different sample holders the time when said valve means starts supplying drawn gas to the sample holder, the time when said valve means stops supplying drawn gas to the sample holder, and the sample interval between when said valve means starts and stops supplying said drawn gas to the sample holder.

* * * * *